United States Patent [19]
Griffith

[11] Patent Number: 5,382,683
[45] Date of Patent: * Jan. 17, 1995

[54] 2-AMINOPROPANAMIDE DERIVATIVES

[75] Inventor: Ronald C. Griffith, Pittsford, N.Y.

[73] Assignee: Fisons Corporation, Rochester, N.Y.

[*] Notice: The portion of the term of this patent subsequent to Jul. 19, 2011 has been disclaimed.

[21] Appl. No.: 870,183

[22] Filed: Apr. 8, 1992

Related U.S. Application Data

[63] Continuation of Ser. No. 610,725, Nov. 7, 1990, abandoned, which is a continuation of Ser. No. 145,943, Jan. 20, 1988, abandoned.

[51] Int. Cl.$^6$ .............................. C07C 233/05
[52] U.S. Cl. ................... 564/196; 564/192; 564/193; 564/194
[58] Field of Search ............... 564/196, 192, 193, 194; 514/626, 630, 625

[56] References Cited

U.S. PATENT DOCUMENTS

| | | | |
|---|---|---|---|
| 2,449,638 | 9/1948 | Bruce | 564/194 |
| 3,692,784 | 9/1972 | Lindberg | 564/196 |
| 4,073,941 | 2/1978 | Lindberg et al. | 514/626 |
| 4,798,687 | 1/1989 | Griffith et al. | 564/138 |

FOREIGN PATENT DOCUMENTS

| | | | |
|---|---|---|---|
| 955508 | 1/1957 | Germany | 564/196 |
| 343388 | 2/1960 | Switzerland | 564/196 |
| 1420067 | 6/1976 | United Kingdom . | |

OTHER PUBLICATIONS

Beilstein's *Handbuch der Organischen Chemie*, 4th ed., 3rd. supplement, (1973) Springer Publications, pp. 3265 and 3276.
CA 64,14162f (Zaheer et al.) (1966).
CA 73,25044n (Novelli et al.) (1970).
CA 77,19586g (Patel et al.) (1972).
CA 85,5705y (Hori et al.) (1976).
CA 96,19744z (Antoniadou-Vyza et al) (1982).

*Primary Examiner*—Shailendra Kumar
*Attorney, Agent, or Firm*—Seidel, Gonda, Lavorgna & Monaco

[57] ABSTRACT

Compounds are provided of the following general structure:

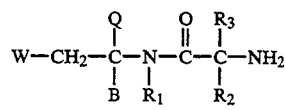

wherein B is hydrogen or lower alkyl ($C_1$–$C_4$), $R_1$ is hydrogen or methyl, $R_2$ is lower alkyl ($C_1$–$C_4$), phenylmethyl or 2-(aminocarbonyl)ethyl, $R_3$ is H or lower alkyl ($C_1$–$C_4$) and where W and Q are independently selected from phenyl or 4-fluorophenyl. They are useful for providing sedative and antiepileptic activity.

1 Claim, No Drawings

2-AMINOPROPANAMIDE DERIVATIVES

This is a continuation of copending application Ser. No. 07/610,725 filed on Nov. 7, 1990 now abandoned, is a continuation of co-pending application Ser. No. 145,943 filed on Jan. 20, 1988, abandoned.

SUMMARY OF THE INVENTION

Novel substituted 2-aminopropanamide derivatives have been prepared and found to possess useful sedative and especially antiepileptic activity.

GENERAL DESCRIPTION

This invention relates to novel 2-aminopropanamide compounds of the following general structure (1):

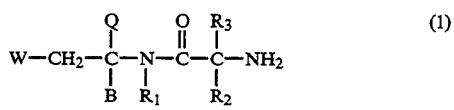

wherein B is hydrogen or lower alkyl ($C_1$-$C_4$), $R_1$ is hydrogen or methyl, $R_2$ is lower alkyl ($C_1$-$C_4$), phenylmethyl or 2-(aminocarbonyl)ethyl, $R_3$ is H or lower alkyl ($C_1$-$C_4$) and where W and Q are independently selected from phenyl or 4-fluorophenyl.

This invention also relates to diastereoisomers, optical isomers and mixtures thereof and to pharmaceutically acceptable acid addition salts of the compounds of general formula (1).

Compounds of this invention possess useful pharmaceutical properties. In particular they possess sedative and antiepileptic properties. Especially useful compounds are those in which B is methyl and W and Q are phenyl.

DETAILED DESCRIPTION

The 2-aminoacetamides of general formula (1) as described fully above are conveniently prepared by suitable amide bond forming reactions from the corresponding amine intermediates of general formula (2):

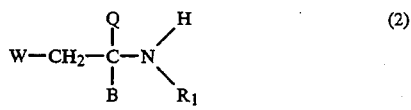

where B is hydrogen, lower alkyl ($C_1$-$C_4$), $R_1$ is hydrogen or methyl, and where W and Q are independently selected from phenyl or 4-fluorophenyl and optical isomers thereof. Most of the amines of general formula (2) are known compounds and may be purchased commercially or conveniently prepared by suitable modifications of the reported procedures. Some of the amines (2) are not known, but are prepared by similar procedures. The preparation of the non-commercially available amines of general formula (2) is described in the "Preparation of Intermediates" Section.

Many amide bond forming reactions may in principle be utilized for the conversion of the amines of general formula (2) to the amides of general formula (1). Two procedures which represent the preferred methods for this conversion are designated Method A and Method B.

Method A consists of direct coupling of commercially available suitably protected amino acid derivatives of formula (3):

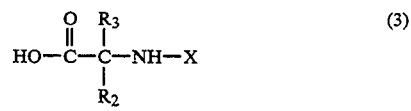

where X is a urethane protecting group preferably benzyloxycarbonyl (CBZ) or t-butyloxycarbonyl (BOC), with an amine of general formula (2), in an inert solvent in the presence of a coupling reagent such as dicyclohexylcarbodiimide with or without 1-hydroxybenzotriazole or other additives to provide coupled products of general formula (4):

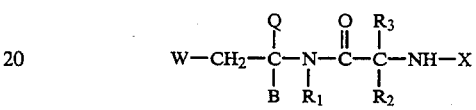

The protecting groups X, are then readily removed by either catalytic hydrogenation for the CBZ groups or treatment with an acid such as trifluoroacetic or hydrochloric acid for the BOC group to provide the compounds of general formula (1).

Method B consists of reacting an amine of general formula (2) with an activated two carbon acid derivative which contains a leaving group alpha to the carbonyl, such as chloropropanoyl chloride, in the presence of an acid acceptor, such as triethylamine, to produce the corresponding 2-chloropropanamide derivative of general formula (5)

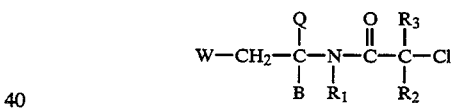

Such an intermediate can be directly reacted with ammonia in a solvent such as a lower alkanol, for example methanol or ethanol, or a chlorinated solvent, for example chloroform or methylene chloride or mixtures thereof to provide the corresponding compounds of general formula (1).

The compounds of general formula (1) possess asymmetric centers, and therefore optical isomers and diastereomeric forms are possible. Such compounds are conveniently prepared from optically active amines of formula (2) and/or optically active protected amino acids of formula (3) by the methods described above.

The compounds of general formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

The compounds of general formula (1) possess useful pharmaceutical properties. In particular they possess useful antiepileptic properties and they possess sedative properties. These activities were assessed by standard methods. Antiepileptic activity was measured by assessing a compound's ability to prevent the hind limb toxic extension component of the seizure in groups of mice induced by maximal electroshock (MES) after oral or intraperitoneal administration according to the procedures of the Epilepsy Branch, NINCDS as published by R. J. Porter, et al., *Cleve. Clin. Quarterly* 1984, 51, 293, and compared to the standard agents dilantin and phenobarbital. Activities ($ED_{50}$'s) in the range of 10–400 m/k after oral administration in this assay system were obtained. Sedative activity was assessed by behavioral observation in groups of mice. Selected compounds exhibited activity in the range of 30–600 m/k in this assay.

An important factor in judging the usefulness of antiepileptic agents is an evaluation of their propensity to produce neurotoxic effects (R. J. Porter, *Cleve. Clin. Quarterly*, 1984, 51, 293). Selected compounds were evaluated in an acute neurological impairment (NI) assay and $NI_{50}$ doses determined in mice essentially according to the procedure of Coughenour, et al., *Pharmac. Biochem. Behav.*, 1977, 6, 351. The oral therapeutic index (TI), that is, the $NI_{50}$ in the neurological impairment assay divided by the $ED_{50}$ in the maximal electroshock assay after oral doses, was calculated. High oral therapeutic indices were observed.

The following non-limiting illustrations and examples are provided to exemplify the preparation of the intermediate amines of formula (2) and their conversion to the novel compounds of general formula (1).

PREPARATION OF INTERMEDIATES

Illustration 1

Preparation of 1,2-Diphenyl-2-propylamine hydrochloride

This compound was prepared by suitable modification of the procedure described by Christol, *Bull. Soc. Chim. Fr.*, 1963, 4, 877, and Ho and Smith, *Tetrahedron*, 1970, 26, 4277 as follows. To a suspension of sodium cyanide (34.3 g, 0.7 mol) in 500 ml of glacial acetic acid and 100 ml of n-butylether at 0° C. was added portionwise 200 ml of concentrated sulfuric acid. The ice bath was removed and a solution of 1,2-diphenyl-2-propanol (106 g, 0.5 m) in 100 ml of n-butylether was added dropwise over a period of 2 hours, then the mixture was stirred for 48 hours. The mixture was poured into 1000 ml of ice, and extracted with chloroform. The extracts were washed with water, dried and evaporated to a solid residue which was stirred with hexane (500 ml), filtered and dried to give 85.35 g (72% yield) of N-formyl-1,2-diphenyl-2-propylamine, mp 97°–99° C. This was suspended in 1 L of 10% HCl and heated to reflux for 2.5 hours. After cooling in air for 1 hour then in an ice bath for 30 minutes, the white solid which had crystallized was collected by filtration and vacuum dried to give 85.9 g (97% yield) of 1,2-diphenyl-2-propylamine hydrochloride, mp 175°–178° C.

Illustration 2

Preparation of 1,2-bis-(4-fluorophenyl)-2-propylamine hydrochloride

By procedures essentially the same as those described in Illustration 1, and by substituting 1,2-bis(4-fluorophenyl)-2-propanol (prepared by the reaction of 4-fluorobenzyl magnesium chloride and 4'-fluoroacetophenone) for 1,2-diphenyl-2-propanol; the corresponding 1,2-bis(4-fluorophenyl)-2-propylamine hydrochloride, mp 188°–189° C., was prepared.

Illustration 3

Preparation of 1,2-Diphenyl-2-butylamine hydrochloride

By procedures essentially the same as those described in Illustration 1, and by substituting 1,2-diphenyl-2-butanol (prepared by the reaction of benzylmagnesium chloride and propiophenone) for 1,2-diphenyl-2-propanol; the corresponding 1,2-diphenyl-2-butylamine hydrochloride, mp 190°–192.5° C., was prepared.

Illustration 4

Preparation of (−)-1,2-Diphenyl-2-propylamine

Racemic 1,2-diphenyl-2-propylamine (86 g, 0.4 mol) was dissolved in 0.5 L 95% ethanol, heated to near reflux and added to a solution of (−)-dibenzoyltartaric acid monohydrate (151.9 g, 0.4 mol) in 0.5 L 95% ethanol also at reflux. A white solid crystallized immediately. The mixture was refluxed for 5 minutes, then allowed to cool to ambient temperature. The solid was collected by filtration and dried to give 86.2 g, $[\alpha]_D = -94.2°$ (C=0.5, $CH_3OH$). The filtrate was saved. The solid was suspended in 0.9 L of 95% ethanol, stirred and heated to reflux for 1 hour, allowed to cool to ambient temperature and the white solid collected by filtration and vacuum dried at 80° C. for 8 hours to give 60.2 g of (−)-1,2-diphenyl-2-propylamine (−)-dibenzoyl tartrate, mp 194°–195° C., $[\alpha]_D = -96.0°$ (C=0.5, $CH_3OH$). 5.0 g of this salt was dissolved in 250 ml $CHCl_3$ and 200 ml 5% $NH_4OH$ shaken vigorously, the layers separated and the organic phase washed with 3×200 ml 5% $NH_4OH$, 2×200 ml $H_2O$ and dried over $MgSO_4$. The solvent was evaporated to give 1.75 g of (−)-1,2-diphenyl-2-propylamine as an oil. The maleate salt was prepared by dissolving this oil in 25 ml of ethyl acetate and adding the solution to a hot solution of maleic acid (1.02 g, 8.87 mmol) in 50 ml of 3/1 ethyl acetate/isopropanol. Upon cooling a white solid crystallized, which was collected by filtration and vacuum dried to give 2.05 g of (−)-1,2-diphenyl-2-propylamine maleate, mp 176°–177° C., $[\alpha]_D = -27.4°$ (C=1, $CH_3OH$).

Illustration 5

Preparation of (+)-1,2-Diphenyl-2-propylamine

The filtrate residue which was saved in Illustration 4, was treated with 1 L $CHCl_3$ and 0.9 L 5% $NH_4OH$, shaken vigorously, the layers separated and the organic phase washed with 4×800 ml 5% $NH_4OH$ and 2×500 ml $H_2O$, then dried over $MgSO_4$ and evaporated to an oil 32.3 g, which is enriched in (+)-1,2-diphenyl-2-propylamine. This oil (32.3 g, 0.153 mol) was dissolved in 200 ml hot 95% ethanol and added to a stirred solution of (+)-dibenzoyl tartaric acid monohydrate (57.55 g, 0.153 mol) in 600 ml of refluxing 95% ethanol. A white solid crystallized immediately, which was stirred at reflux for 5 minutes, then allowed to cool to ambient temperature. The solid was collected by filtration and vacuum dried at 80° C. for 8 hours to give 71.6 g of (+)-1,2-diphenyl-2-propylamine (+)-dibenzoyltartrate, mp 197°–198° C., $[\alpha]_D = +95.8°$ (C=0.5, $CH_3OH$). 5.0 g of this salt was dissolved in 250 ml $CHCl_3$ and 200 ml 5% $NH_4OH$, shaken vigorously, the layers separated and the organic phase washed with 3×200 ml 5% $NH_4OH$ and 2×200 ml $H_2O$ and dried over $MgSO_4$. The solvent was evaporated to give 1.75 g of (+)-1,2- diphenyl-2-propylamine as an oil. The maleate salt was prepared by dissolving this oil in 25 ml ethyl acetate and adding the solution to a hot solution of maleic acid (1.02 g, 8.78 mmole) in 50 ml 3/1 ethyl acetate/isopropanol. Upon cooling a white solid crystallized, which was collected by filtration and vacuum dried to give 2.06 g of (+)-1,2-diphenyl-2-propylamine maleate, mp 177°-178° C., $[\alpha]_D = +27.3°$ (C=1, CH$_3$OH).

Illustration 6

Preparation of N-Methyl-1,2-diphenyl-2-propylamine hydrochloride

N-formyl-1,2-diphenyl-2-propylamine (23.6 g, 0.1 mol) was added to a stirred suspension of LiAlH$_4$ (15.0 g, 0.395 mol) in 1 L of dry tetrahydrofuran. After 2 hours the mixture was heated at 35° C. for 22 hours, then refluxed for 2 hours, and allowed to cool to room temperature. Water was added to decompose the excess LiAlH$_4$, and the mixture filtered to remove the solid salts. Evaporation of the solvent gave 23.0 g of the crude product as a yellow oil. This was dissolved in 180 ml of ethyl acetate and 20 ml of isopropanol and acidified with HCl gas. Upon standing a white solid crystallized which was collected by filtration and vacuum dried at 65° C. to give 21.7 g (84%) of N-methyl-1,2-diphenyl-2-propylamine hydrochloride, mp 200°-201° C.

Illustration 7

Preparation of N-Methyl-1,2-diphenylethylamine

To a stirred two phase solution of 1,2-diphenylethylamine (30.0 g, 0.15 mol) in 300 ml of methylene chloride and 500 ml of water was added sodium carbonate (23.9 g, 0.225 mol) and the solution was cooled to 10° C. under nitrogen. Ethyl chloroformate (21.5 ml, 0.225 mol) was added dropwise over a one hour period. The reaction was warmed to ambient temperature and stirred at that temperature for 3 hours. The phases were separated and the aqueous phase was extracted with methylene chloride (75 ml). The combined methylene chloride extracts were washed with 1N HCl (200 ml), brine (200 ml), dried and evaporated to a white solid, 40.3 g. Recrystallization from cyclohexane gave N-carboethoxy-1,2-diphenylethylamine, mp 74°-75° C.

To a stirred suspension of lithium aluminum hydride (12.4 g, 0.032 mol) in 300 ml of tetrahydrofuran at 0 C. under nitrogen was added dropwise a solution of N-carboethoxy-1,2-diphenylethylamine (35.0 g, 0.13 mmol) in 200 ml of tetrahydrofuran. The mixture was heated to reflux for 8 hours. The mixture was cooled in an ice-water bath and water (13 ml), 15% NaOH (13 ml) and water (39 ml) were carefully added to the mixture. The mixture was warmed to ambient temperature and the precipitated salts were removed by filtration through celite. Removal of solvent gave N-methyl-1,2-diphenylethylamine, 26.8 g as a colorless oil.

Treatment of this oil with maleic acid in ethyl acetate and methanol gave N-methyl-1,2-diphenylethylamine maleate, mp 129°-131° C.

Example 1

Preparation of (2S)-2-Amino-3-phenyl-N-(1,2-diphenyl-1-methylethyl)propanamide hydrochloride To a stirred solution of 1,2-diphenyl-2-propylamine (10.2 g, 0.048 mol) in 400 ml of chloroform under nitrogen were added N-CBZ-L-phenylalanine (14.36 g, 0.048 mol) and then a solution of dicyclohexylcarbodiimide (9.90 g, 0.048 mol) in 130 ml of chloroform and the mixture stirred for 20 hours. The precipitated solid was removed by filtration and the solvent evaporated. Ethyl acetate (200 ml) was added to the residue and the insoluble material was removed by filtration. Ethyl acetate (300 ml) was added to the filtrate. The ethyl acetate solution was washed with 1N HCl (2×200 ml), brine (2×150 ml) and dried over MgSO$_4$. Removal of solvent gave 28.72 g of a yellow oil. This oil was dissolved in 350 ml of methanol and 35 ml of 10% HCl, and hydrogenated at 40 psi in a Parr apparatus over 3.0 g of 10% Pd/C catalyst for 3.5 hours. The catalyst was removed by filtration and the solvent evaporated. Water (300 ml) was added to the residue, the solution was basified to pH 11 with 50% NaOh, and extracted with chloroform (2×200 ml). The combined chloroform extracts were dried over MgSO$_4$ and the solvent was evaporated to give 21.23 g of a yellow oil. This oil was purified by chromatography on silica gel with a Prep 500 HPLC, eluting with ethyl acetate-hexanes (1:1). Pure fractions were combined and evaporated to give 10.5 g of an oil. This oil was dissolved in ethyl acetate (75 ml) and the solution was treated with gaseous HCl. The solvent was removed and the residue was dissolved in methanol and the solvent evaporated (2×). The resulting white solid was triturated with ethyl acetate (75 ml) and recrystallized from ethyl acetate (100 ml) and 2-propanol (0.1 ml) to give 3.7 g of (2S)-2-amino-3-phenyl-N-(1,2-diphenyl-1-methylethyl)-propanamide hydrochloride, mp 157°-158° C.

Example 2

Preparation of (2R)-2-Amino-3-phenyl-N-(1,2-diphenyl-1-methylethyl)propanamide hydrochloride By procedures essentially the same as those described in Example 1 and by substituting N-CBZ-D-phenylalanine for N-CBZ-L-phenylalanine; the corresponding (2R)-2-amino-3-phenyl-N-(1,2-diphenyl-1-methylethyl)propanamide hydrochloride mp. 156°-157° C., was prepared.

Example 3

Preparation of (2S)-2-Amino-N-(1,2-diphenyl-1-methylethyl)propanamide hydrochloride By procedures essentially the same as those described in Example 1 and by substituting N-CBZ-L-alanine for N-CBZ-L-phenylalanine; the corresponding (2S)-2-amino-N-(1,2-diphenyl-1-methylethyl)propanamide hydrochloride, mp. 115°-116° C. was prepared.

Example 4

Preparation of (2R)-2-Amino-N-(1,2-diphenyl-1-methylethyl)propanamide hydrochloride By procedures essentially the same as those described in Example 1 and by substituting N-CBZ-D-alanine for N-CBZ-L-phenylalanine; the corresponding (2R)-amino-N-(1,2-diphenyl-1-methylethyl)propanamide hydrochloride, mp. 115°-116° C., was prepared.

Example 5

Preparation of 2-Amino-N-(1,2-diphenyl-1-methylethyl)-2-methylpropanamide

By procedures essentially the same as those described in Example 1 and by substituting N-CBZ-α,α-dimethylglycine for N-CBZ-L-Phenylalanine; the corresponding 2-amino-N-(1,2-diphenyl-1-methylethyl)-2-methylpropanamide mp 117°–118° C., was prepared.

Example 6

Preparation of (2S)-2-Amino-4-(aminocarbonyl)-N-(1,2-diphenyl-1-methylethyl)butanamide maleate By procedures essentially the same as those described in Example 1 and by substituting N-CBZ-L-glutamine for N-CBZ-L-phenylalanine; the corresponding (2S)-2-amino-4-(aminocarbonyl)-N-(1,2-diphenyl-1-methylethyl)butanamide maleate, mp. 158° C., was prepared.

Example 7

Preparation of (2R)-2-Amino-4-(aminocarbonyl)-N-(1,2-diphenyl-1-methylethyl)butanamide maleate By procedures essentially the same as those described in Example 1 and by substituting N-CBZ-D-glutamine for N-CBZ-L-phenylalanine; the corresponding (2R)-2-amino-4-(aminocarbonyl)-N-(1,2-diphenyl-1-methylethyl)butanamide maleate, mp. 168° C., was prepared.

Example 8

Preparation of (2S)-2-Amino-N-[1,2-bis(4-fluorophenyl)-1-methylethyl]propanamide To a stirred solution of 1,2-bis(4-fluorophenyl)-2-propylamine (11.07 g, 0.045 mol) in 200 ml of chloroform under nitrogen, were added N-CBZ-L-alanine (10.0 g, 0.045 mol) and then a solution of dicyclohexylcarbodiimide (9.90 g, 0.05 mol) in 100 ml of chloroform, and the mixture was stirred for 16 hours. The precipitated solid was removed by filtration and the solvent evaporated. The residue was treated with ethyl acetate (100 ml), filtered, an additional 300 ml of ethyl acetate added, and then washed with 1% cold HCl (100 ml), brine (2×100 ml), dried over $MgSO_4$, and the solvent evaporated. The residue was dissolved in 450 ml of methanol and 35 ml of 10% HCl and hydrogenated at 40 psi in a Parr apparatus over 3.0 g of 5% Pd/C catalyst for 3 hours. The catalyst was removed by filtration, the solvent evaporated and the residue dissolved in water (200 ml) and chloroform (300 ml), basified to pH 11 with 50% NaOH, shaken and separated. The aqueous phase was extracted with chloroform (2×200 ml), and the combined organic phases were washed with water (2×200 ml), and dried over $MgSO_4$. Removal of solvent gave a white solid. This solid was recrystallized from cyclohexane/hexane and then from hexane/ethanol, and vacuum dried to give 1.5 g of (2S)-2-amino-N-[1,2-bis(4-fluorophenyl)-1-methylethyl]propanamide, mp. 134°–135° C.

I claim:
1. 2-Amino-N-(1,2-diphenyl-1-methylethyl)propanamide or a pharmaceutically acceptable acid addition salt thereof.

* * * * *